(12) United States Patent
DeCarlo

(10) Patent No.: US 8,968,345 B2
(45) Date of Patent: Mar. 3, 2015

(54) SURGICAL INTRODUCER WITH INDICATORS

(75) Inventor: Arnold V. DeCarlo, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1435 days.

(21) Appl. No.: 12/369,192

(22) Filed: Feb. 11, 2009

(65) Prior Publication Data

US 2009/0240273 A1 Sep. 24, 2009

Related U.S. Application Data

(60) Provisional application No. 61/038,914, filed on Mar. 24, 2008.

(51) Int. Cl.
*A61B 17/32* (2006.01)
*A61B 5/107* (2006.01)
*A61B 5/06* (2006.01)
*A61B 17/06* (2006.01)
*A61B 19/00* (2006.01)
*A61B 5/01* (2006.01)
(Continued)

(52) U.S. Cl.
CPC ............. *A61B 5/1076* (2013.01); *A61B 5/01* (2013.01); *A61B 5/061* (2013.01); *A61B 5/441* (2013.01); *A61B 17/06109* (2013.01); *A61B 19/46* (2013.01); *A61B 19/5212* (2013.01); *A61B 2017/00022* (2013.01); *A61B 2017/00084* (2013.01); *A61B 2017/00199* (2013.01); *A61B 2019/461* (2013.01); *A61B 2019/462* (2013.01); *A61B 2019/464* (2013.01); *A61B 2019/467* (2013.01); *A61B 2019/4857* (2013.01)
USPC ................. 606/167; 606/32; 606/33; 606/34; 606/35; 606/36; 606/50; 606/51; 606/52; 606/184; 600/114; 600/137; 600/173; 600/345; 604/164; 604/534

(58) Field of Classification Search
USPC .............. 606/32–52, 184; 600/137, 114, 173, 600/345; 604/164, 534
See application file for complete search history.

(56) References Cited

U.S. PATENT DOCUMENTS

| 1,266,945 A | 5/1918 | Hickey |
| 3,710,781 A | 1/1973 | Huthcins, IV et al. |
| 3,908,461 A | 9/1975 | Turpen |

(Continued)

OTHER PUBLICATIONS

In di ca tor The American Heritage® Dictionary of the English Language, Fourth Edition copyright © 2000 by Houghton Mifflin Company. Updated in 2009. Published by Houghton Mifflin.*

*Primary Examiner* — William Thomson
*Assistant Examiner* — Victor Shapiro

(57) ABSTRACT

A surgical introducer including a body portion, a shaft and a sensor is disclosed. The body portion includes a reference indicator. The shaft defines a longitudinal axis and is positionable adjacent the body portion. The shaft is rotatable with respect to the body portion and includes a longitudinal indicator and a circumferential indicator. The sensor is disposed in mechanical cooperation with a distal portion of the shaft and is adapted to provide physiological data pertaining to a surgical worksite. At least a portion of the sensor is substantially aligned with the circumferential indicator. Rotation of the shaft with respect to the body portion causes displacement between the circumferential indicator and the reference indicator. Longitudinal movement of the shaft with respect to the body portion causes displacement between the longitudinal indicator and the reference indicator.

10 Claims, 5 Drawing Sheets

(51) Int. Cl.
*A61B 5/00* (2006.01)
*A61B 17/00* (2006.01)

(56) References Cited

U.S. PATENT DOCUMENTS

| | | | |
|---|---|---|---|
| 3,939,823 A | 2/1976 | Kaye et al. | |
| 3,946,724 A | 3/1976 | La Balme | |
| 3,960,018 A | 6/1976 | Change et al. | |
| 4,023,562 A | 5/1977 | Hynecek et al. | |
| 4,227,420 A | 10/1980 | Lamadrid | |
| 4,274,423 A | 6/1981 | Mizuno et al. | |
| 4,397,335 A | 8/1983 | Doblar et al. | |
| 4,423,740 A | 1/1984 | Castle et al. | |
| 4,471,786 A | 9/1984 | Inagaki et al. | |
| 4,512,357 A | 4/1985 | Earl | |
| 4,567,773 A | 2/1986 | Cooper et al. | |
| 4,683,757 A | 8/1987 | Adams et al. | |
| 4,724,843 A | 2/1988 | Fisher | |
| 4,825,876 A | 5/1989 | Beard | |
| 4,869,265 A | 9/1989 | McEwen | |
| 4,938,068 A | 7/1990 | Clements | |
| 5,097,841 A | 3/1992 | Moriuchi et al. | |
| 5,105,820 A | 4/1992 | Moriuchi et al. | |
| 5,146,929 A | 9/1992 | Sawhill | |
| 5,150,104 A | 9/1992 | Thomas et al. | |
| 5,280,789 A | 1/1994 | Potts | |
| 5,336,206 A * | 8/1994 | Shichman | 604/534 |
| 5,456,724 A | 10/1995 | Yen et al. | |
| 5,464,388 A | 11/1995 | Merte et al. | |
| 5,526,820 A | 6/1996 | Khoury | |
| 5,540,100 A | 7/1996 | von Berg | |
| 5,658,306 A * | 8/1997 | Kieturakis et al. | 606/184 |
| 5,725,364 A | 3/1998 | Mirazita | |
| 5,796,007 A | 8/1998 | Panagotopulos et al. | |
| 5,935,083 A | 8/1999 | Williams | |
| 5,964,714 A | 10/1999 | Lafontaine | |
| 5,970,978 A | 10/1999 | Aviv et al. | |
| 5,976,105 A | 11/1999 | Marcove et al. | |
| 6,019,728 A | 2/2000 | Iwata et al. | |
| 6,036,655 A | 3/2000 | Aviv et al. | |
| 6,053,860 A * | 4/2000 | Brooks | 600/137 |
| 6,086,542 A | 7/2000 | Glowa et al. | |
| 6,106,476 A | 8/2000 | Corl et al. | |
| 6,142,958 A | 11/2000 | Hammarström et al. | |
| 6,162,182 A | 12/2000 | Cole | |
| 6,176,831 B1 | 1/2001 | Voss et al. | |
| 6,224,585 B1 | 5/2001 | Pfeiffer | |
| 6,228,034 B1 | 5/2001 | Voss et al. | |
| 6,234,958 B1 * | 5/2001 | Snoke et al. | 600/114 |
| 6,275,717 B1 * | 8/2001 | Gross et al. | 600/345 |
| 6,296,615 B1 | 10/2001 | Brockway et al. | |
| 6,355,003 B1 | 3/2002 | Aviv et al. | |
| 6,367,366 B1 | 4/2002 | Bloom et al. | |
| 6,379,308 B1 | 4/2002 | Brockway et al. | |
| 6,394,986 B1 | 5/2002 | Millar | |
| 6,493,237 B1 | 12/2002 | Moody et al. | |
| 6,500,115 B2 * | 12/2002 | Krattiger et al. | 600/173 |
| 6,554,781 B1 | 4/2003 | Carter et al. | |
| 6,572,543 B1 | 6/2003 | Christopherson et al. | |
| 6,645,143 B2 | 11/2003 | VanTassel et al. | |
| 6,666,826 B2 | 12/2003 | Salo et al. | |
| 6,673,022 B1 | 1/2004 | Bobo et al. | |
| 6,676,600 B1 | 1/2004 | Conero et al. | |
| 6,688,179 B2 | 2/2004 | Potter et al. | |
| 6,691,579 B2 | 2/2004 | Orr et al. | |
| 6,695,789 B2 | 2/2004 | Thede et al. | |
| 6,706,005 B2 | 3/2004 | Roy et al. | |
| 6,740,047 B2 | 5/2004 | Holmes et al. | |
| 6,743,180 B1 | 6/2004 | Van Bockel | |
| 6,749,574 B2 | 6/2004 | O'Keefe | |
| 6,758,657 B1 | 7/2004 | McNaull et al. | |
| 6,860,857 B2 | 3/2005 | Norén et al. | |
| 6,892,095 B2 | 5/2005 | Salo | |
| 6,916,286 B2 * | 7/2005 | Kazakevich | 600/173 |
| 6,926,674 B2 | 8/2005 | Tenerz et al. | |
| 6,957,588 B1 | 10/2005 | Kicher et al. | |
| 6,968,741 B2 | 11/2005 | Orr et al. | |
| 6,974,422 B1 | 12/2005 | Millar | |
| 6,983,546 B2 | 1/2006 | Li | |
| 6,994,695 B1 | 2/2006 | Millar | |
| 7,025,727 B2 | 4/2006 | Brockway et al. | |
| 7,052,465 B1 | 5/2006 | Lunak et al. | |
| 7,056,319 B2 | 6/2006 | Aliperti et al. | |
| 7,073,509 B2 | 7/2006 | Tenerz et al. | |
| 7,097,620 B2 | 8/2006 | Corl et al. | |
| 7,137,954 B2 | 11/2006 | Thede et al. | |
| 7,137,958 B2 | 11/2006 | Wada et al. | |
| 7,150,713 B2 | 12/2006 | Shener et al. | |
| 7,172,561 B2 | 2/2007 | Grinberg | |
| 7,174,789 B2 | 2/2007 | Orr et al. | |
| 2002/0049394 A1 | 4/2002 | Roy et al. | |
| 2002/0162397 A1 | 11/2002 | Orr et al. | |
| 2003/0079548 A1 | 5/2003 | Potter et al. | |
| 2003/0158487 A1 | 8/2003 | Thede et al. | |
| 2003/0176814 A1 | 9/2003 | Li | |
| 2004/0059230 A1 | 3/2004 | Thede et al. | |
| 2004/0118212 A1 | 6/2004 | Orr et al. | |
| 2004/0133132 A1 | 7/2004 | Chappuis | |
| 2004/0133168 A1 * | 7/2004 | Salcudean et al. | 604/164.13 |
| 2004/0186396 A1 | 9/2004 | Roy et al. | |
| 2004/0254504 A1 | 12/2004 | Li | |
| 2005/0010210 A1 * | 1/2005 | Bee et al. | 606/41 |
| 2005/0049501 A1 | 3/2005 | Conero et al. | |
| 2005/0154320 A1 | 7/2005 | Froelich et al. | |
| 2006/0036184 A1 | 2/2006 | Tenzer et al. | |
| 2006/0036221 A1 | 2/2006 | Watson | |
| 2006/0081166 A1 | 4/2006 | Montgomery et al. | |
| 2006/0117856 A1 | 6/2006 | Orr et al. | |
| 2006/0200028 A1 | 9/2006 | Evans | |
| 2006/0200121 A1 * | 9/2006 | Mowery | 606/41 |
| 2006/0224223 A1 | 10/2006 | Podhajsky et al. | |
| 2007/0016084 A1 | 1/2007 | Denault | |
| 2007/0021674 A1 | 1/2007 | Thede et al. | |
| 2007/0043374 A1 | 2/2007 | Evans | |

* cited by examiner

SURGICAL INTRODUCER WITH INDICATORS

CROSS-REFERENCE TO RELATED APPLICATIONS

This application claims the benefit of priority to U.S. Provisional Application Ser. No. 61/038,914 entitled "SURGICAL INTRODUCER WITH INDICATORS" filed Mar. 24, 2008 by Arnold V. DeCarlo, which is incorporated by reference herein.

BACKGROUND

1. Technical Field

The present disclosure relates generally to surgical instrumentation, and methods of use thereof, for ascertaining physiological data pertaining to a surgical worksite. More particularly, the present disclosure relates to a surgical introducer including a sensor, as well as methods of use thereof, to detect and determine various attributes of tissue.

2. Background of Related Art

Either prior to or during the course of a surgical procedure, it is often desirable to ascertain physiological data pertaining to a surgical worksite, a patient's internal cavities and/or tissues, such as blood vessels, tissue masses, and tumors. By ascertaining this data, a clinician is able to more efficiently, safely, and expeditiously accomplish the goals of the procedure. This physiological data may include information regarding the presence of any such tissues, as well as various attributes thereof; including but not being limited to their size, shape, location, and/or orientation.

Various instruments, systems and methods for ascertaining such physiological data are known in the art. For example, electrosurgical instruments and magnetic resonance or ultrasonic imaging technology may be use to detect the presence and/or investigate one or more of the exemplary attributes enumerated above. While the instruments currently available are useful for such purposes, they can be expensive, cumbersome and slow.

SUMMARY

A surgical introducer including a body portion, a shaft and a sensor is disclosed. The body portion includes a reference indicator. The shaft defines a longitudinal axis and is positionable adjacent the body portion. The shaft is rotatable with respect to the body portion and includes a longitudinal indicator and a circumferential indicator. The sensor is disposed in mechanical cooperation with a distal portion of the shaft and is adapted to provide physiological data pertaining to a surgical worksite. At least a portion of the sensor is substantially aligned with the circumferential indicator. Rotation of the shaft with respect to the body portion causes displacement between the circumferential indicator and the reference indicator and allows a user to determine the circumferential movement of the sensor. Longitudinal movement of the shaft with respect to the body portion causes displacement between the longitudinal indicator and the reference indicator and allows a user to determine the longitudinal movement of the sensor.

The present disclosure also relates to a method of ascertaining physiological data. The method includes the steps of providing a surgical introducer including a body portion, a shaft and a sensor. The body portion includes a reference indicator. The shaft defines a longitudinal axis and is positionable adjacent the body portion. The shaft is rotatable with respect to the body portion. The shaft includes a longitudinal indicator and a circumferential indicator. The sensor is disposed in mechanical cooperation with the shaft and at least a portion of the sensor is substantially aligned with the circumferential indicator. The method also includes the steps of positioning the surgical introducer within tissue. Taking a first measurement with the sensor when the surgical introducer is in an initial position and moving the shaft with respect to the body portion such that the surgical introducer is in a second position.

BRIEF DESCRIPTION OF THE DRAWINGS

The accompanying drawings, which are incorporated in, and constitute a part of this specification, illustrate embodiments of the disclosure and, together with a general description of the disclosure given above and the detailed description of the embodiment(s) given below, serve to explain the principles of the disclosure, wherein.

DETAILED DESCRIPTION

Figure 1:
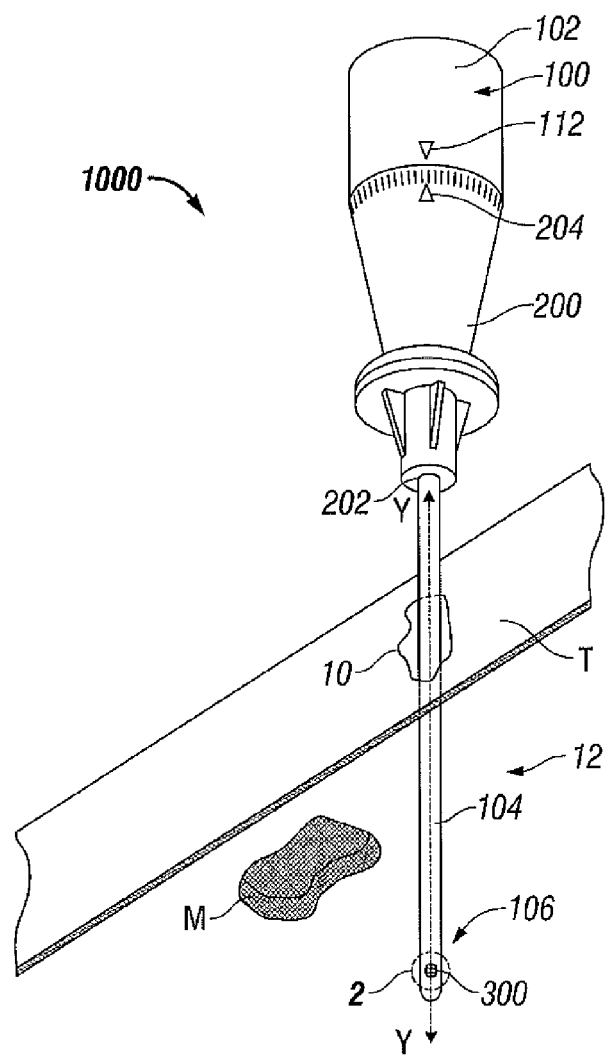
FIG. 1 is a front, perspective view of a surgical introducer in accordance with an embodiment of the present disclosure, and shown in an initial position within tissue.

Various embodiments of the presently disclosed surgical introducer, and method of using the same, are described in detail with reference to the drawings wherein like references numerals identify similar or identical elements. In the drawings and in the description which follows, the term "proximal" refers to the end of the surgical introducer that is closest to the operator during use, while the term "distal" refers to the end of the surgical introducer that is furthest from the operator, as is traditional and conventional in the art.

Figure 2:
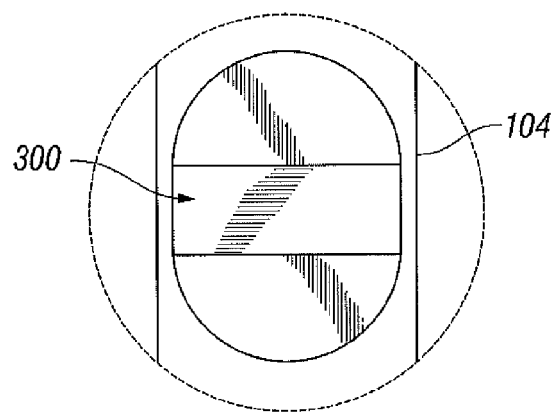
FIG. 2 is an enlarged view of a sensor for use with the surgical introducer of FIG. 1.
Figure 3:
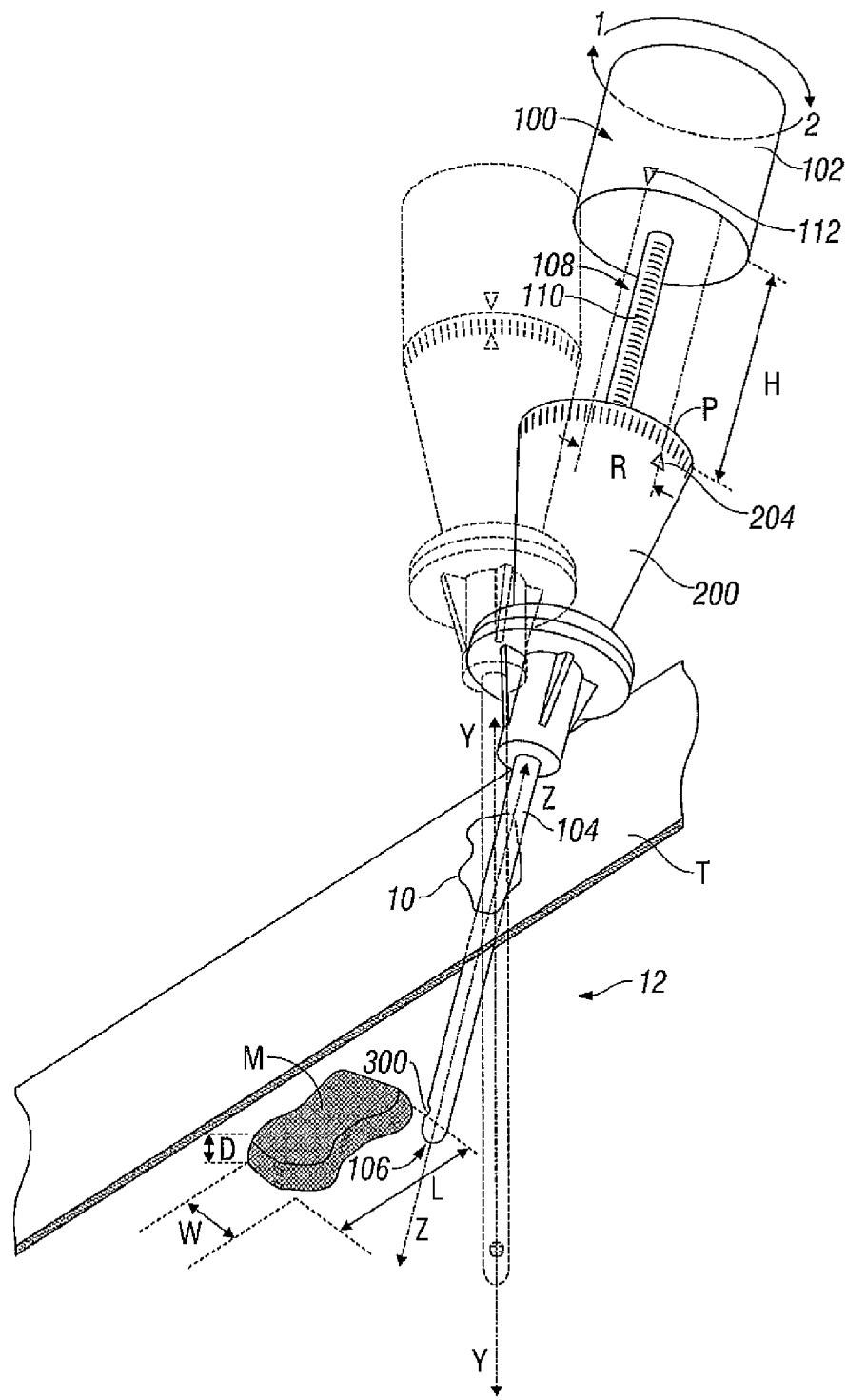
FIG. 3 is a front, perspective view of the surgical introducer of FIG. 1 shown in a subsequent configuration within tissue.
Figure 4:
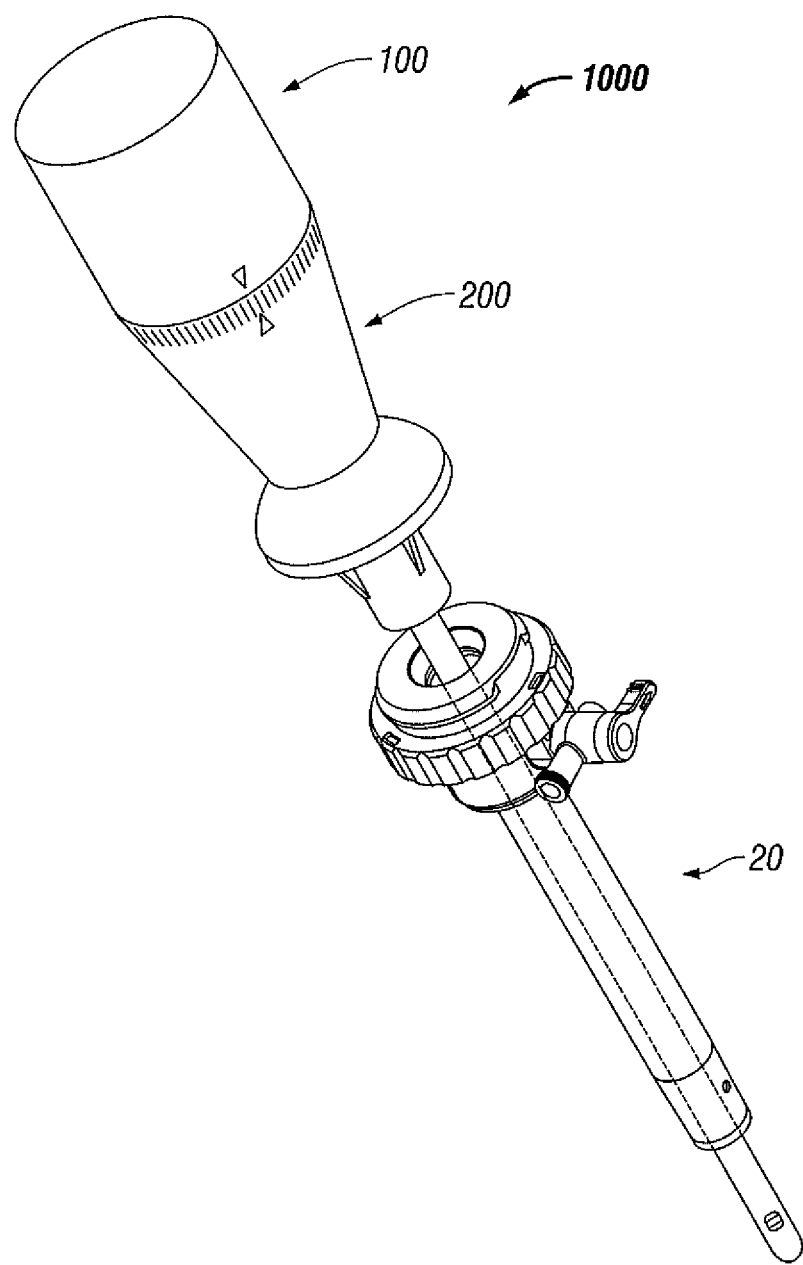
FIG. 4 is a front, perspective view of the surgical introducer of FIG. 1 shown inserted into a cannula assembly.

Referring now to the drawings, FIGS. 1-3 illustrate a surgical introducer 1000 in accordance with an embodiment of the present disclosure. The surgical introducer 1000 is positionable within a tissue tract 10 formed in tissue "T." The tissue tract 10 may be either pre-existing, e.g., an incision created through the use of a scalpel, or may be created by the surgical introducer 1000 itself, as described below. Alternatively, the surgical introducer 1000 may be configured for percutaneous introduction through a surgical access assembly, such as the cannula assembly 20 seen in FIG. 4.

The surgical introducer is movable between an initial position, illustrated in FIG. 1, and one or more subsequent positions, an example of which is depicted in FIG. 3, as discussed in detail below. The surgical introducer 1000 includes a shaft 100, a body portion 200 and a sensor 300 (e.g., a pressure transducer). Shaft 100 includes a proximal portion 102 and a substantially rigid element 104 extending distally therefrom and defining longitudinal axis "Y-Y."

Each of the proximal portion 102 of the shaft 100 and the body portion 200 is generally configured for being gripped by a user and may be formed of any suitable material.

Figure 5:
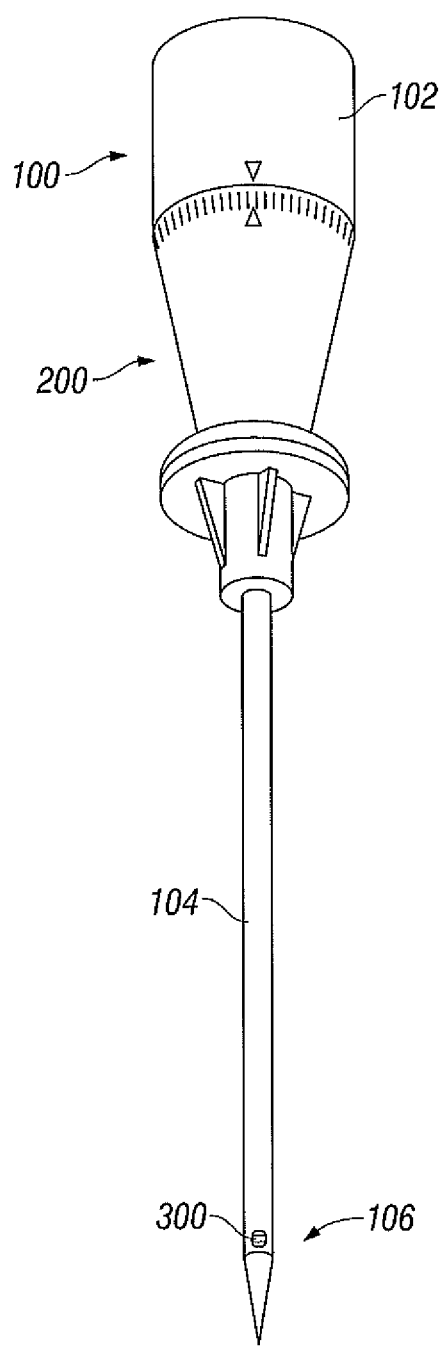
FIG. 5 is a front view of one embodiment of the surgical introducer of FIG. 1 including a shaft having a substantially incisive distal end.

In the embodiments illustrated in FIGS. 1-3, shaft 100 includes a distal end 106 that is substantially blunt to facilitate atraumatic insertion of the surgical introducer 1000 into the tissue tract 10. Alternatively, the shaft 100 may include a substantially incisive distal end 106, as seen in FIG. 5, to facilitate creation of the tissue tract 10.

The shaft 100 is configured for insertion into an opening 202 formed in the body portion 200 and extending therethrough such that the shaft 100 is longitudinally movable with respect to body portion 200, as well as rotatably movable in the direction of arrows 1 and 2 (see FIG. 3), relative to the body portion 200. The shaft 100 includes a first (longitudinal) indicator 108 extending along at least a portion of its length to help allow the user to determine the longitudinal displacement of the shaft 100 from the body portion by measuring the distance "H" therebetween, if any. The first indicator 108 may be printed, embossed or otherwise visible to the user. In the embodiment of FIGS. 1-3, the first indicator 108 includes distance markings (e.g., inches, centimeters, etc.) formed on an outer surface 110 of the shaft 100 to help enable the user to measure the distance "H."

The shaft 100 also includes a second (circumferential) indicator 112 to allow the user to determine the circumferential displacement "R" of the shaft 100 relative to the body portion 200, if any. The circumferential displacement "R" is determined by measuring the distance between the second indicator 112 and a reference indicator 204 (disposed on the body portion 200) upon movement of the shaft 100 with respect to the body portion 200. As with the first indicator 108, the second indicator 112 and the reference indicator 204 may each be printed, embossed or otherwise visible to the user. In the embodiment of FIGS. 1-3, the body portion 200 further includes markings extending about its periphery "P" to help enable the user to measure the rotation of the shaft 100 in terms of degrees or relative to a reference marker (not shown).

The sensor 300 is adapted to provide physiological data pertaining to the surgical worksite 12 through the manipulation of the surgical introducer 1000. This physiological data may include information regarding the presence of tissue, e.g., a tissue mass "M," as well as various attributes thereof, including but not being limited to the size and shape of the tissue, as well as the tissue's location and/or orientation within the surgical worksite 12.

The sensor 300 is associated with the distal end 106 of the shaft 100 such that longitudinal and/or rotational movement of the shaft 100 relative to the body portion 200 effectuates corresponding movement of the sensor 300. Accordingly, by measuring the respective longitudinal and circumferential displacement, "H" and "R," of the shaft 100 relative to the body portion 200, the longitudinal and circumferential displacement of the sensor 300 within the surgical worksite 12, the sensor's 300 corresponding position, can also be determined. To further help ascertain the position of the sensor 300 within the surgical worksite 12, at least a portion of the sensor 300 may be substantially aligned with the second indicator 112.

The sensor 300 may be any mechanism or structure suitable for the intended purpose of providing a user of the surgical introducer 1000 with physiological data pertaining to the surgical worksite 12, such as information pertaining to the tissue mass "M", for example. The sensor 300 may be adapted to measure pressure or heat, and/or to provide the user with a visual image of the surgical worksite 12.

Figure 6:
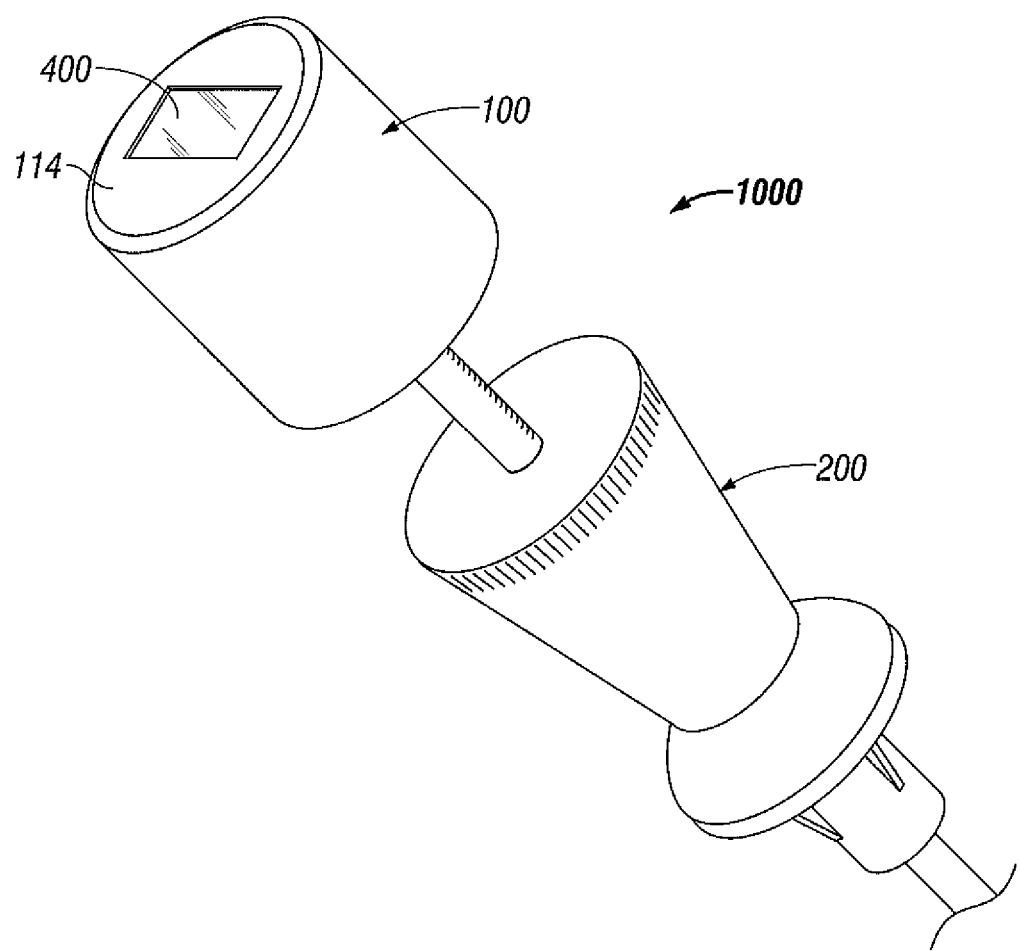
FIG. 6 is a top, perspective view of another embodiment of the surgical introducer of FIG. 1 including a display located at a proximal end of the shaft.

In one embodiment, the sensor 300 is adapted to detect and/or measure a pressure differential by comparing one or more measured pressures. The existence of a pressure differential may be communicated to the user in any suitable manner. For example, the surgical introducer 1000 may be adapted to provide tactile or audible feedback to the user, and/or the sensor 300 may be in communication with a display 400 to provide the user with visual notification, as illustrated in FIG. 6. The display 400 may be disposed in any suitable location, including but not being limited to a proximal end 114 of the shaft 100 such that the display 400 is viewable by the user while the sensor 300 is within tissue.

The present disclosure also includes a method where a user can employ the surgical introducer 1000 to ascertain physiological data pertaining to the surgical worksite 12, as well as information regarding various attributes of the tissue mass "M" located therein.

Prior to the introduction of the surgical introducer 1000 to the surgical worksite 12, the surgical introducer 1000 is set to an initial position. In this position (FIG. 1), the respective proximal portion 102 of the shaft 100 and the body portion 200 are in an abutting relationship, and the second indicator 112 is substantially aligned with the reference indicator 204, i.e., "H" and "R" are both equal to zero. Thereafter, the surgical introducer 1000 is moved into a second position, an example of which is illustrated in FIG. 3. To achieve each subsequent position, the shaft 100 may be separated from the body portion 200, the shaft 100 may be rotated relative to the body portion 200, and/or the surgical introducer 1000 may be displaced along one or more axes extending in a transverse relation to the longitudinal axis "Y-Y" defined by the shaft 100, e.g., the axis "Z-Z" along which the surgical introducer 1000 is positioned in FIG. 3.

The ability of the user to separate and approximate the shaft 100 and the body portion 200, to rotate the shaft 100 relative to the body portion 200, and/or to displace the surgical introducer 1000 along a number of transverse axes, e.g., axis "Z-Z", allows for positioning of the sensor 300 in the surgical worksite 12 to ascertain information from any area thereof. Upon insertion of the surgical introducer 1000 into the surgical worksite 12, an initial measurement is taken with the sensor 300 such as, for example, an initial pressure measurement. Thereafter, the sensor 300 may be repositioned within the surgical worksite 12 as described above, to take subsequent pressure measurements. By comparing the initial and subsequent pressure measurements, the user can detect the presence of the tissue mass "M," as the pressure measured by the sensor 300 in the presence of the tissue mass "M" will be appreciably different than the pressure measured by the sensor 300 in the absence of the tissue mass "M." Upon the detection of such a pressure differential, the surgical introducer 1000 may notify the user, e.g., audibly or visually, as discussed above, and thereby alert the user to the presence of the tissue mass "M."

In the embodiment shown in FIG. 1, the sensor 300 is not necessarily positioned adjacent tissue mass "M." The surgical introducer 1000 may then be moved (e.g., by separating the shaft 100 from the body portion 200, by rotating the shaft 100 relative to the body portion 200, and by displacing the surgical introducer 1000 along any number of axes) such that the sensor 300 is adjacent/can sense tissue mass "M." Upon positioning the sensor 300 as illustrated in FIG. 3, the user will be notified of a change in pressure, and will thereby be alerted to the presence of the tissue mass "M." The user may then note or record the location of the sensor 300 within the tissue "T" through reference to the first indicator 108, the second indicator 112 and the reference indicator 204, e.g., by measuring the longitudinal displacement "H" and the circumferential displacement "R." By noting the location of the sensor 300 in the second position relative to its location in the initial position, the user can repeatedly and accurately place the sensor 300 in the same location within the tissue "T" (e.g., if the position of the reference indicator 204 is maintained).

After locating the tissue mass "M," additional information regarding the tissue mass "M" can be ascertained. By moving the surgical introducer 1000 and noting the locations in which the pressure measurements taken by the sensor 300 are different (or the same), information regarding the size and shape of the tissue mass "M" can be ascertained, as well as information concerning its shape and/or orientation within the surgical worksite 12. In particular, the length "L" of the tissue mass "M" may be determined by separating and approximating the shaft 100 and body portion 200 and the width "W" of the tissue mass "M" may be determined by rotating the shaft 100 relative to the body portion 200. In addition, the depth "D" of the tissue mass "M," as well as its orientation, may be determined by manipulating the surgical introducer 1000 along one or more axes, e.g., axis "Z-Z" as shown in FIG. 3 or extending in transverse relation to the axis "Y-Y" defined by the shaft 102. It is envisioned that body portion 200 includes indicia thereon to help a user determine the orientation of the shaft 100 in relation to the transverse axis.

While the above is a complete description of various embodiments of the present disclosure, alternatives, modifications and equivalents may be employed. Therefore, the above description should not be construed as limiting, but rather as illustrative of the principles of the disclosure made herein, and those skilled in the art may envision other adaptations without departing from the scope and spirit of the present disclosure or the claims appended hereto.

What is claimed is:

1. A method of ascertaining physiological data, comprising the steps of:
    providing a surgical introducer, the surgical introducer including a body portion, a shaft, and a sensor;
    positioning the surgical introducer within tissue;
    measuring a physiological attribute of the tissue with the sensor when the surgical introducer is in an initial position, wherein, when the surgical introducer is in the initial position, a circumferential indicator disposed on an outer surface of the shaft and a reference indicator disposed on an outer surface of the body portion are substantially aligned;
    moving the shaft with respect to the body portion such that the surgical introducer is in a second position, wherein moving the shaft includes concurrently rotating the shaft and longitudinally translating the shaft; and
    measuring a physiological attribute of the tissue with the sensor when the surgical introducer is the second position.

2. The method of claim 1, wherein the step of moving the shaft includes at least one of rotating the shaft and longitudinally translating the shaft.

3. The method of claim 1, further comprising the step of comparing the measurements taken in the initial position and the second position.

4. The method of claim 1, further comprising the step of determining a circumferential movement of the sensor via measuring a displacement between the circumferential indicator of the shaft and the reference indicator of the body portion.

5. The method of claim 1, further comprising the step of determining a longitudinal movement of the sensor via measuring a displacement between a longitudinal indicator of the shaft and the reference indicator of the body portion.

6. The method of claim 4, further comprising the step of determining a longitudinal movement of the sensor via measuring a displacement between a longitudinal indicator of the shaft and the reference indicator.

7. The method of claim 1, wherein the step of providing a surgical introducer includes providing a surgical introducer having a shaft including an incisive distal end to facilitate insertion of the surgical introducer into tissue.

8. The method of claim 7, further comprising the step of creating an insertion in tissue with the distal end of the shaft.

9. The method of claim 1, wherein the step of positioning the surgical introducer within tissue comprises inserting the shaft through an opening in the body portion.

10. A method of ascertaining physiological data, comprising the steps of:
    providing a surgical introducer, the surgical introducer including:
        a body portion including a reference indicator disposed on an outer surface of the body portion;
        a shaft defining a longitudinal axis and being positionable adjacent the body portion and being rotatable with respect to the body portion, the shaft including a longitudinal indicator and a circumferential indicator, the circumferential indicator disposed on an outer surface of the shaft, wherein the circumferential indicator and the reference indicator are substantially aligned when the surgical introducer is in the initial position; and
        a sensor disposed in mechanical cooperation with the shaft, at least a portion of the sensor being substantially aligned with the circumferential indicator;
    positioning the surgical introducer within tissue;
    taking a first measurement with the sensor when the surgical introducer is in an initial position;
    moving the shaft with respect to the body portion such that the surgical introducer is in a second position, wherein moving the shaft includes concurrently rotating the shaft and longitudinally translating the shaft; and
    measuring a physiological attribute of tissue when the surgical introducer is the second position.

* * * * *